United States Patent [19]
Lindqvist

[11] Patent Number: 5,998,675
[45] Date of Patent: Dec. 7, 1999

[54] PROCESS FOR PREPARING TERTIARY ALKYL ETHERS

[75] Inventor: Petri Lindqvist, Porvoo, Finland

[73] Assignee: Neste Oy, Espoo, Finland

[21] Appl. No.: 09/091,651

[22] PCT Filed: Dec. 19, 1996

[86] PCT No.: PCT/FI96/00677

§ 371 Date: Jun. 22, 1998

§ 102(e) Date: Jun. 22, 1998

[87] PCT Pub. No.: WO97/23437

PCT Pub. Date: Jul. 3, 1997

[30] Foreign Application Priority Data

Dec. 22, 1995 [FI] Finland .................................. 956255

[51] Int. Cl.$^6$ ................................................ C07C 41/06
[52] U.S. Cl. ........................................ 568/697; 568/699
[58] Field of Search .................................. 568/697, 647, 568/699

[56] References Cited

U.S. PATENT DOCUMENTS

| | | | |
|---|---|---|---|
| 5,015,782 | 5/1991 | Harandi et al. | 568/697 |
| 5,245,087 | 9/1993 | Zahn | 568/697 |
| 5,248,836 | 9/1993 | Bakshi et al. | 568/697 |
| 5,491,267 | 2/1996 | Frey et al. | 568/647 |

FOREIGN PATENT DOCUMENTS

| | | |
|---|---|---|
| 0 590 632 A1 | 4/1994 | European Pat. Off. |
| WO 93/19032 | 9/1993 | WIPO |
| WO 94/08927 | 4/1994 | WIPO |

*Primary Examiner*—Shailendra Kumar
*Assistant Examiner*—Sreeni Padmanabhan
*Attorney, Agent, or Firm*—Birch, Stewart, Kolasch & Birch, LLP

[57] ABSTRACT

A process for preparing tertiary alkyl ethers comprises the steps of reacting $C_{4-7}$ isoolefins of an olefinic hydrocarbon feedstock with an alkanol in the presence of a first catalyst in a reaction zone to form a reaction mixture containing a tertiary alkyl ether or a mixture of tertiary alkyl ethers, feeding the reaction mixture to a distillation column, distilling the reaction mixture and recovering the alkyl ether(s) with the bottoms product of the distillation. An azeotrope formed by unreacted $C_4$ hydrocarbons and the alkanol is withdrawn as an overhead product of the distillation. According to the invention, a part of the liquid flow of the column is withdrawn to form a side drawoff, and the side drawoff is recirculated to the reaction zone. As a result, the conversion of the reactive $C_6$ hydrocarbons is increased and the operating cost of the ethers process is reduced.

11 Claims, 1 Drawing Sheet

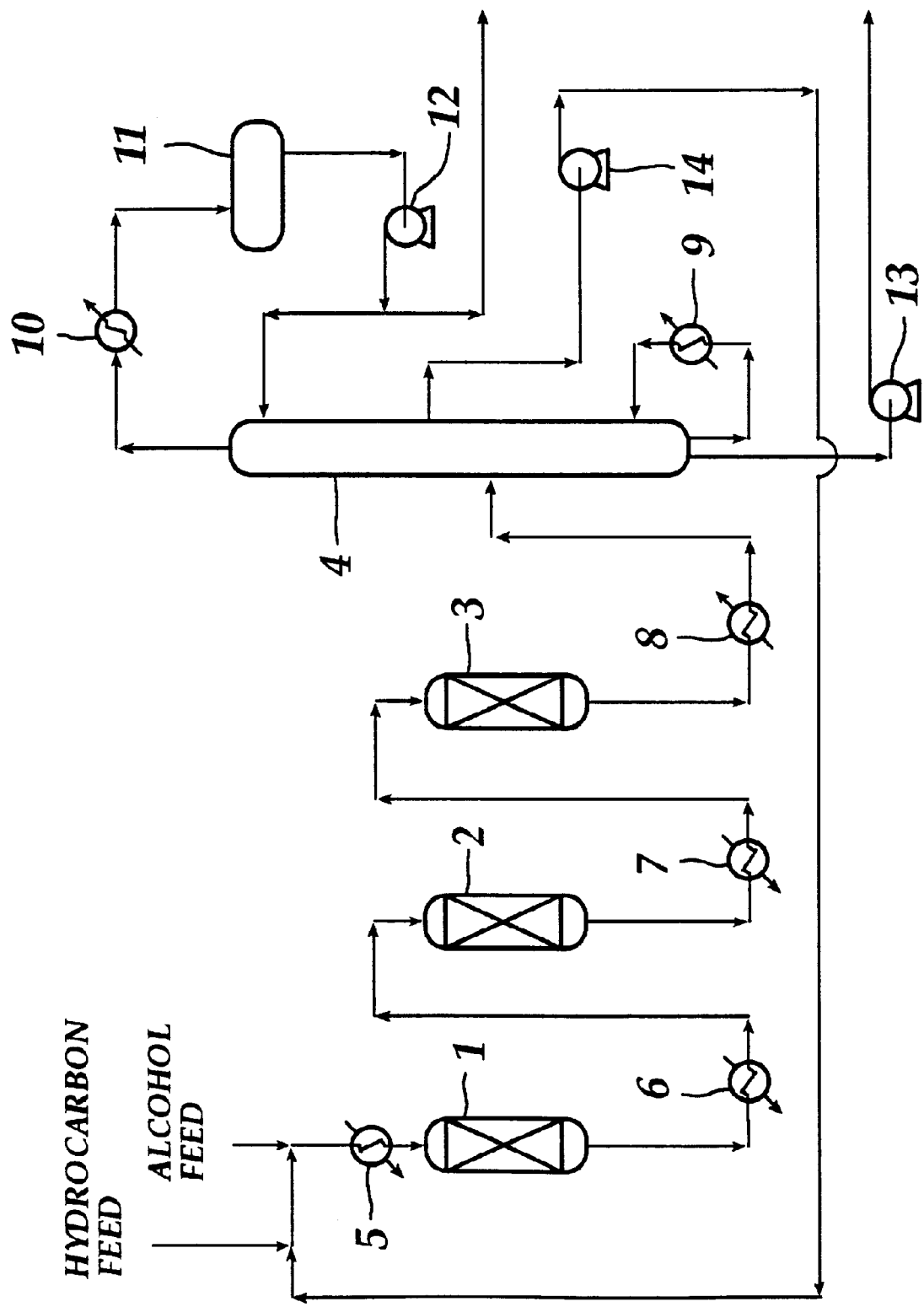

5,998,675

PROCESS FOR PREPARING TERTIARY ALKYL ETHERS

This application is the national phase under 35 U.S.C. §371 of prior PCT International Application No. PCT/FI96/00677 which has an International filing date of Dec. 19, 1996 which designated the United States of America, the entire contents of which are hereby incorporated by reference.

BACKGROUND OF THE INVENTION

1. Field of the Invention

The present invention concerns a process for preparing tertiary alkyl ether products which are used, in particular, as components of motor fuels. The products contain, methyl t-butyl ether, ethyl t-butyl ether, t-amyl methyl ether or t-amyl ethyl ether, or mixtures thereof, and possibly heavier tertiary alkyl ethers. According to the process, isoolefins, in particular the $C_4$–$C_7$ isoolefins, of an olefinic hydrocarbon feedstock are reacted with a suitable alkanol in order to prepare the corresponding ethers. These ethers are removed together with the bottoms product of the distillation reaction system and, if necessary, they are further processed in order to prepare a motor fuel component. Unreacted alkanol is removed with the overhead product of the distillation.

2. Description of Related Art

Tertiary alkyl ethers are added to gasoline in order to improve the anti-knocking characteristics thereof and to reduce the concentration of harmful components in the exhaust gases. The oxygen-containing ether group of these compounds has been found favourably to improve the combustion process of automotive engines. Suitable alkyl tert-alkyl ethers are methyl t-butyl ether (MTBE), ethyl t-butyl ether (ETBE), t-amyl methyl ether (TAME), t-amyl ethyl ether (TAEE) and t-hexyl methyl ethers (THME), to mention a few examples. These ethers are prepared by etherification of isoolefins with monovalent aliphatic alcohols (alkanols). The reactions can be carried out in a fixed bed reactor, in a fluidized bed reactor, in a tubular reactor or in a catalytic distillation column.

The etherification reaction is an exothermic equilibrium reaction, and maximum conversion is determined by the thermodynamic equilibrium of the reaction system. To use TAME as an example, it is possible to obtain an about 90% conversion by carrying out reaction and separation in a reactive distillation column, whereas only a 65 to 70% conversion is obtainable in a fixed bed reactor.

Ion exchange resins are the most common etherification catalysts. Generally the resin used comprises a sulfonated polystyrene/divinyl benzene based cation exchange resin (sulfonated polystyrene cross-linked with divinylbenzene) having particle sizes in the range from 0.1 to 1 mm.

Two types of TAME processes have been commercially available for some time. The first one comprises fixed bed reactors, columns for product separation by distillation and a methanol separation unit. In the other process, the product distillation is replaced by a catalytic distillation unit, which substantially improves the TAME conversion, as mentioned above.

A third completely novel etherification process is described in our International Patent Application WO 93/19031. This novel process comprises a catalytic distillation unit which has been modified by transferring the catalyst conventionally placed in the distillation column into a separate external reactor which is being fed from the product separation distillation unit. The side reactor product is recycled back to the same product separation distillation unit. According to an embodiment of that process described in our international patent application WO 93/19032, the product distillation of the catalytic distillation reactor system is operated in such a way that most, and preferably practically all, of the alkanol which is removed with the distillate is bound to the inert $C_4$ hydrocarbons of the distillate, forming an azeotrope with them. The product is recovered from the bottom of the column and it comprises a mixture of TAME and heavier ethers.

The process described in our international patent applications mentioned above can also be used for preparing lower alkyl ethers, such as methyl t-butyl ether (MTBE) and ethyl t-butyl ether (ETBE), and mixed ether products containing such ethers.

A suitable feedstock for the above-mentioned processes for preparing tertiary alkyl ethers is Fluidized Catalytic Cracking (FCC) Gasoline containing $C_{4-7}$ hydrocarbons, a substantial portion, generally at least 5%, typically about 7 to 30 wt-%, of which comprises reactive $C_{4-7}$ isoolefins. These reactive isoolefins include the following compounds: isobutene, 2-methyl-1-butene, 2-methyl-2-butene, 2-methyl-1-pentene, 2-methyl-2-pentene, 2,3-dimethyl-1-butene, 2,3-dimethyl-2-butene, 2-ethyl-1-butene, 2-methyl-2-hexene, 2,3-dimethyl-1-pentene, 2,3-dimethyl-2-pentene, 2,4dimethyl-1-pentene, 2-ethyl-1-pentene and 2-ethyl-2-pentene. Other suitable hydrocarbon feedstocks for etherification processes are formed by Pyrolysis $C_5$ Gasoline, Thermofor Catalytic Cracking (TCC) Gasoline, Residual Catalytic Cracking (RCC) Gasoline and Coker Gasoline.

Although the above-mentioned novel etherification process will provide excellent conversion rates of the reactive $C_4$'s and $C_5$'s, the conversion of the reactive $C_6$'s to the corresponding tertiary alkyl ethers (e.g., THME, tert-hexyl methyl ether, THEE, tert-hexyl ethyl ether) is less than 50%. Depending on the process configuration it can even be less than 40 or 30%. In a mixture containing $C_4$, $C_5$ and $C_6$-based ethers and the corresponding non-reactive hydrocarbons, an increase of the amount of $C_6$ ethers would significantly reduce the vapor pressure of the ether products, improve the octane number thereof and, considering the fact that the alkanol is a more inexpensive component than the gasoline, increase the cost efficiency of the process.

SUMMARY OF THE INVENTION

The present invention aims at eliminating the problems associated with the prior art by providing a novel process for producing tertiary alkyl ethers from an olefinic hydrocarbon feedstock while increasing the conversion of reactive $C_6$ hydrocarbons to over 50% and maintaining high conversion rates (over 90%) of reactive $C_4$ and $C_5$ hydrocarbons.

The present invention is primarily based upon the novel etherification process described in international patent application WO 93/19032. In particular, the hydrocarbon feedstock and at least one alkanol are fed into a reaction zone, wherein the components of the feed, viz., the alkanol(s) and the reactive isoolefins, are reacted with each other in order to form a product containing tertiary alkyl ethers. The reaction mixture is continuously subjected to fractionation in a distillation column. A bottoms product mainly containing the alkyl ethers formed and substantially all of the unreacted hydrocarbons is withdrawn from the distillation, whereas the overhead product mainly contains an azeotrope formed by the non-reactive (inert) feed hydrocarbons, in particular the non-reactive $C_4$ hydrocarbons, and alkanol not consumed by the etherification reaction.

According to the present invention the feed stream containing the hydrocarbons together with the alcohol is combined with a recycle stream from the fractionator (distillation column) before it is being fed into the etherification reaction zone. Surprisingly, it has turned out that by recycling from the distillation column a drawoff at a rate of 10 to 500%, preferably about 50 to 200%, of the fresh feed stream and combining it with the fresh feed, it becomes possible to increase the conversion of the reactive $C_6$'s to over 65% compared with less than 50% if the side drawoff is subjected to etherification separately.

In particular the present invention comprises the following steps:

reacting $C_{4-7}$ isoolefins of an olefinic hydrocarbon feedstock with an alkanol in the presence of a first catalyst in at least one reaction zone to form a reaction mixture containing a tertiary alkyl ether or a mixture of tertiary alkyl ethers, feeding the reaction mixture to a distillation column at a feed point between the bottom and the top of the column, subjecting said reaction mixture to distillation in the distillation column, recovering the alkyl ethers and $C_{5-7}$ hydrocarbons with the bottoms product of the distillation, withdrawing as an overhead product of the distillation an azeotrope formed by unreacted $C_4$ hydrocarbons and said alkanol, withdrawing a part of the liquid flow of the column from above the feed point of the reaction mixture to form a side drawoff, and recirculating the side drawoff to the reaction zone.

BRIEF DESCRIPTION OF THE DRAWING

Next, the invention will be described in more detail with the aid of the attached drawing, which depicts a simplified scheme of an etherification process according to the present invention, comprising three prereactors and a product separation column.

DETAILED DESCRIPTION OF THE INVENTION

The production of the ether according to the present invention can be carried out in a conventional etherification system comprising a number of reactors in a cascade connected to at least one distillation column designated for product separation. Typically, in such a process configuration, the feed hydrocarbons together with the alcohol (methanol or ethanol) and the recycle stream from the fractionator are fed to the reaction zone, which comprises at least two reactors. The greater the ratio of heavier hydrocarbons to light hydrocarbons, the more reactors are needed. The feed is first adjusted to the specific reaction temperature used before feeding to first etherification reactor. The effluent from the first reactor is cooled and fed to a second etherification reactor. The effluent from the second reactor is optionally cooled and fed to a third (fourth etc.) etherification reactor. The effluent of the last reactor is then heated and fed to the main fractionator, which is operated according to the principles laid down in WO 93/19032, i.e. so that the distillate consists of mainly $C_4$ hydrocarbons and the alcohol, which is in azeotropic concentration in the distillate. The amount of unreactive feed $C_4$'s therefore fixes the amount of distillate. A side drawoff is taken out from the distillation column above the feed point and fed to the first reactor via a heat exchanger. The bottom product consists of unreacted hydrocarbons and the ethers formed.

In the above embodiment, the fresh feed, the alkanol and the side drawoff are mixed together before feeding into the etherification zone. It is also possible to feed one (e.g. the alkanol) or all of the three streams separately into the etherification zone. In that case, the side drawoff is preferably cooled before being fed into the reaction zone.

The term "alkanol" includes lower alkyl alcohols capable of forming azeotropes with saturated and unsaturated hydrocarbons, in particular $C_3$ to $C_7$ hydrocarbons, of the hydrocarbon feedstock. As specific examples of the alkanols, the following can be mentioned: methanol, ethanol, n-propanol, i-propanol, n-butanol, i-butanol and t-butanol. Methanol and ethanol are particularly preferred.

The term "olefinic hydrocarbon feedstock", is intended to cover all hydrocarbon feedstocks, which contain an isoolefin or a mixture of isoolefins which can be etherified to form tertiary alkyl ethers. In particular, the following feedstocks are preferred: FCC Gasoline, FCC Light Gasoline, Pyrolysis $C_5$ Gasoline, TCC Gasoline, RCC and Coker Gasoline. The feed can also comprise a mixture of two or more olefinic hydrocarbon feedstocks, such as a mixture of FCC Light Gasoline and a pyrolysis $C_5$ cut. The proportion of the various $C_4$ to $C_7$ isoolefins will, of course, to a large extent determine the composition of the ether product.

Of the above feedstocks, FCC, RCC and TCC are preferred because these hydrocarbon cuts can be used as such, possibly after the removal of heavier cuts ($C_{8+}$). The use of Pyrolysis Gasoline requires that the light cut and the $C_{6+}$ cut be removed before it can be fed into the process. Up to some 10% of the $C_{6+}$ cut can be included in the resulting hydrocarbon mixture, called a Pyrolysis $C_5$ Gasoline, so as to ensure that substantially all of the reactive $C_5$'s of the Pyrolysis Gasoline are present in the olefinic feedstock. This feedstock will also contain reactive aliphatic $C_{6+}$ hydrocarbons. Pyrolysis Gasoline is particularly rich in isoprene (up to 10 wt-%) and other diolefins, which can be converted to mono-unsaturated hydrocarbons by selective hydrogenation. This will greatly improve the value of this cut as a feedstock for etherification, in particular in combination with any of the above mentioned cracking gasoline cuts.

The attached drawing gives an overview of a preferred embodiment of the process according to the present invention.

Thus, in the test arrangement depicted in the drawing, the hydrocarbon feedstock, the alkanol, and a side stream from distillation column 4 are mixed together, the mixture is heated and fed through the reactor section 1, 2. The hydrocarbon feedstock may, for instance, be a hydrocarbon fraction containing isoolefins, such as a hydrocarbon cut of a cat cracker, containing a mixture of isoolefins. The reactors consist of three reactors filled with ion exchange resin beds. The reactors can be fixed or fluidized bed or tubular reactors. The reactors may be arranged in series (in a cascade), as shown in the figure, or in parallel. If there are more than two reactors they may also be arranged in series/parallel. Because of the reaction there is a temperature rise in the prereactors in the range from about 5 to about 15° C. depending on the amount of isoolefins and the efficiency of the reactor insulation. From the reactors the mixture is conducted to distillation column 4. The location of the feed point is defined below more specifically. At the bottom of the distillation column 4 there is a reboiler 9. The distillation column can be a packed column or one provided with valve, sieve or bubble-cap trays. The overhead of the column is removed via a condenser 10 to a reflux drum 11, from which the overhead is removed by means of a pump 12. A part of the overhead is forwarded to further processing and a part thereof is returned to the distillation column. Ethers are removed with the bottoms product. In addition to the ether, the bottoms product also contains unreacted $C_{4+}$ hydrocarbons. The reflux ratio of the column is preferably from about 1 to 500. Even greater ratios can be used in pilot plant equipments. According to the invention, the reflux ratio is adjusted so that the distillate amount removed from the process at least substantially corresponds to the amount of $C_4$ hydrocarbons of the feed.

From the distillation column 4 a side stream is taken and mixed with fresh hydrocarbon and alkanol feeds as described above. The side drawoff comprises some 10 to 500%, preferably about 50 to about 200% of the fresh feed. The pressure of the side stream is increased by pump 14 because the distillation is typically carried out at a lower pressure than the reaction. The side stream is preferably taken from a tray which is located below trays having alkanol K-values less than 1. The effluent of the reactors (distillation column feed) is fed to a plate having an alkanol K-value greater than 1. As a result of this arrangement, the alkanol gets more enriched in the vapor phase than do the hydrocarbons. The side drawoff makes up 40 to 90%, typically about from 60 to about 70% of the total liquid flow within the column.

The distillation is carried out at a pressure generally ranging from about 1.1 to 20 bars and the etherification reaction at 6 to 40 bars. When preparing TAME, the temperature at the top of the distillation column is about 40 to 70° C., typically about 50 to 60° C., and at the bottom of the column about 100 to 150, typically about 120 to 130° C.

As mentioned above, according to the present invention the distillation column of the reactive distillation unit is operated in such a way that the alkanol is heavier than the hydrocarbons at the top of the distillation column. Therefore, the alkanol not bound to the hydrocarbons in the form of an azeotrope will tend to flow downwards within the column. At the same time the vapor-liquid-equilibrium between $C_5$ and heavier hydrocarbons and the alkanol at the bottom of the column is maintained at such a level that the alkanol is lighter than the hydrocarbons. This causes the alkanol to flow upwards from the bottom of the column. Thus, the alkanol will circulate within the distillation system between the top and the bottom of the column. By fitting a reaction bed in the distillation column or by conducting a side stream from the column through a reaction bed in a side reactor, an alkanol consuming reaction can be created which will remove the alkanol from the system.

The alkanols, in particular methanol and ethanol, form azeotropes with the hydrocarbons of the feedstock. The heavier the hydrocarbons, the greater the alkanol concentration of the hydrocarbon-alkanol-azeotrope. According to the present invention, in order to minimize the amount of unreacted alkanol removed from the distillation process, substantially only the $C_4$-hydrocarbon-alkanol azeotropes are taken as an overhead product. These azeotropes are the lightest hydrocarbon-alkanol azeotropes and have the smallest alkanol concentrations.

Thus, according to the present invention, the amount of unreacted alkanol can be controlled by adjusting the amount of $C_4$ hydrocarbons in the feed so that it correlates with the amount of alkanol. The less there are $C_4$ hydrocarbons in the feed, the less distillate can be removed and the less alkanol is removed from the process. By increasing the amount of $C_4$ hydrocarbons in the feed the distillate flow rate can be increased without any change of the relative amount of free unreacted alkanol in the overhead product. Therefore, if desired, $C_4$ hydrocarbons (or even $C_3$ hydrocarbons) can deliberately be added to the process so that the intended effect is achieved.

When operating the process according to the invention, the alkanol concentration of the bottoms product of the column can easily be reduced to as small a value as desired. In the case of methanol, it is possible to reduce its concentration in the bottoms product to below 100 ppm. The amount of alkanol in the distillate will correspond to the amount bound by the azeotrope, only. The composition of the azeotrope and, thus, the amount of alkanol removed depends on the hydrocarbon composition of the overhead product and the operating pressure of the distillation. To mention an example based on the production of TAME: if $C_4$ hydrocarbons make up the main part (over 90%) of the overhead product, there will remain some 0.1 to 5.0% by weight of methanol depending on the distillation pressure and the amount of $C_5$ hydrocarbons. The more $C_5$ hydrocarbons are included in the overhead product, the more methanol will be removed with it (there may be less than 90% by weight of the $C_4$ hydrocarbons in the overhead product).

The above-described etherification is preferably carried out in the presence of a conventional cation exchange resin. However also different kinds of zeolites can also be used as etherification catalysts. Thus, the resin may contain sulfonic acid groups and it can be obtained by polymerization or copolymerization of aromatic vinyl compounds followed by sulfonation. Examples of aromatic vinyl compounds suitable for preparing polymers of copolymers are: styrene, vinyl toluene, vinyl naphthalene, vinyl ethyl-benzene, methyl styrene, vinyl chlorobenzene and vinyl xylene. The acid cation exchange resin typically contain some 1.3 to 1.9 sulfonic acid groups per aromatic nucleus. Preferred resins are based on copolymers of aromatic monovinyl compounds with aromatic polyvinyl compounds, particularly, divinyl compounds, in which the polyvinyl benzene content is from about 1 to 20 wt-% of the copolymer. The ion exchange resin preferably has a granular size of about 0.15 to 1 mm.

In addition to the above resins, perfluorosulfonic acid resins which are copolymers of sulfonyl fluorovinyl ethyl and fluorocarbon can be used.

The invention is preferably carried out in connection with the MTBE, ETBE, TAME and the TAEE processes.

In connection with the TAME process, the overhead product obtained can be forwarded to a MTBE unit. Since it contains some impurities ($C_5$ hydrocarbons, as far as the MTBE process is concerned), the overhead product can be introduced either in the feed of the MTBE unit, which means that the $C_5$ hydrocarbons remain in the MTBE product, or to the methanol washing unit of the MTBE unit. In the latter case the $C_5$ hydrocarbons end up in the raffinate stream of the MTBE unit (which contains mainly $C_4$ hydrocarbons).

Alternatively, the overhead product of the distillation can—because it contains only minute amounts of methanol and because the overhead is very small compared to the feed—also be combined with the bottoms product of the distillation in order to form a gasoline component. If necessary, the mixture is subjected to an additional treatment. According to a preferred embodiment of the invention, the $C_4$ hydrocarbon content of the feed is, however, deliberately kept so small that the mixture of the overhead and the bottoms products can be used as such as a component of motor fuels.

Considerable benefits are achieved by means of the invention. Thus, not only is the conversion rate of the reactive $C_6$'s greatly increased, the present invention also reduces the capital investment of the etherification process by simplifying the equipment, and increases the yield of produced ethers compared to the state of art. The operating costs are also lowered by reduced utility (steam, water) usage.

The following working example will clarify the invention:

EXAMPLE

Preparation of Tertiary Methyl and Ethyl Ethers

Using the process configuration of FIG. 1, methyl and ethyl ethers were prepared from an olefinic hydrocarbon feed as follows:

Distillation
column: Inner diameter 160 mm, height 11,000 mm, filled with column packing. The number of packing layers was 6.
Reactors: Inner diameter 154.1 mm, height 1,150 mm. Filled with the catalyst DOWEX M-32
Location of
side drawoff: Between the second and third packing layer.
Feed point: Between the fourth and fifth packing layer.
For the preparation of the methyl ethers, two reactors in a cascade were used, whereas the ethyl ethers were prepared using three reactors in a cascade.

In both cases an olefinc feed stream containing 30 kg hydrocarbons/h (compositions shown in Tables 1 and 2 and an alcohol (amounts shown in Tables 1 and 2) were mixed together and heated. Then, a side drawoff stream was combined therewith and the modified feed stream thus obtained was conducted through the reactors. As a result of the exothermal etherification reaction, the temperature increased in the reactors with 5 to 15° C., depending on the efficiency of the heat insulation. The reaction mixture obtained was conducted to a distillation column and subjected to distillation.

When preparing methyl ethers, the feed temperature of the reactors was 39° C. and temperatures of the reaction mixture streams at the outlet of the reactors were 46.5 and 40° C., respectively. In case of ethanol, the feed streams were fed into the reactors at 59, 59 and 49° C., respectively, whereas the temperatures of the reaction mixture streams at the outlets of the reactors were 69, 61 and 50.5° C., respectively.

Distillate was recovered from the top of the distillation column (composition shown in Tables 1 and 2).

The composition of the side drawoff withdrawn from the column is also indicated in Tables 1 and 2. The pressure of the side drawoff stream were increased with a pump before they were conducted to the reactors.

The reflux ratios of the distillation were, in case of MeOH feed, 100 and, in case of EtOH feed, 20.

The results obtained are shown in Tables 1 and 2.

TABLE 1

| | 1 Feed | | 2 MeOH feed | | 10 Side draw | | 11 Top Product | | 12 Bottom product | |
|---|---|---|---|---|---|---|---|---|---|---|
| | Mass Flow | Mass-% | Mass Flow | Mass-% | Mass Flow | Mass-% | Mass Flow | Mass-% | Mass Flow | Mass-% |
| H2O | 0.00 | 0.00 | 0.00 | 0.05 | 0.00 | 0.00 | 0.00 | 0.00 | 0.00 | 0.00 |
| DME | 0.00 | 0.00 | 0.00 | 0.00 | 0.00 | 0.00 | 0.00 | 0.01 | 0.00 | 0.00 |
| trans-2-butene | 0.63 | 2.11 | 0.00 | 0.00 | 2.06 | 4.29 | 0.63 | 88.16 | 0.00 | 0.00 |
| 3-methyl-1-butene | 0.04 | 0.14 | 0.00 | 0.00 | 1.44 | 2.99 | 0.01 | 1.47 | 0.03 | 0.10 |
| Iso-pentane | 5.20 | 17.33 | 0.00 | 0.00 | 28.62 | 59.62 | 0.04 | 5.96 | 5.16 | 16.18 |
| 2-methyl-1-butene | 0.46 | 1.52 | 0.00 | 0.00 | 0.05 | 0.10 | 0.00 | 0.00 | 0.01 | 0.04 |
| n-pentane | 4.22 | 14.08 | 0.00 | 0.00 | 6.88 | 14.33 | 0.00 | 0.13 | 4.22 | 13.26 |
| 2-methyl-2-butene | 3.27 | 10.89 | 0.00 | 0.00 | 0.45 | 0.94 | 0.00 | 0.01 | 0.34 | 1.06 |
| n-pentene | 0.65 | 2.18 | 0.00 | 0.00 | 1.03 | 2.15 | 0.00 | 0.01 | 0.65 | 2.05 |
| 2,3-dimethyl-butene | 3.04 | 10.12 | 0.00 | 0.00 | 0.50 | 1.05 | 0.00 | 0.00 | 3.04 | 9.53 |
| 2-methyl-1-pentene | 0.66 | 2.21 | 0.00 | 0.00 | 0.05 | 0.10 | 0.00 | 0.00 | 0.38 | 1.18 |
| 3-methyl-pentene | 1.79 | 5.96 | 0.00 | 0.00 | 0.16 | 0.33 | 0.00 | 0.00 | 1.79 | 5.61 |
| MEOH | 0.00 | 0.00 | 2.58 | 99.95 | 6.62 | 13.78 | 0.03 | 4.26 | 0.00 | 0.00 |
| 2-methyl-2-pentene | 3.37 | 11.23 | 0.00 | 0.00 | 0.06 | 0.12 | 0.00 | 0.00 | 1.00 | 3.13 |
| N-hexane | 2.34 | 7.80 | 0.00 | 0.00 | 0.07 | 0.15 | 0.00 | 0.00 | 2.34 | 7.35 |
| benzene | 0.46 | 1.53 | 0.00 | 0.00 | 0.02 | 0.03 | 0.00 | 0.00 | 0.46 | 1.44 |
| TAME | 0.00 | 0.00 | 0.00 | 0.00 | 0.01 | 0.02 | 0.00 | 0.00 | 4.91 | 15.41 |
| 2-methyl-heksane | 1.80 | 6.02 | 0.00 | 0.00 | 0.00 | 0.00 | 0.00 | 0.00 | 1.80 | 5.66 |
| N-heptane | 2.06 | 6.88 | 0.00 | 0.00 | 0.00 | 0.00 | 0.00 | 0.00 | 2.06 | 6.47 |
| TAOH | 0.00 | 0.00 | 0.00 | 0.00 | 0.00 | 0.00 | 0.00 | 0.00 | 0.01 | 0.02 |
| THME | 0.00 | 0.00 | 0.00 | 0.00 | 0.00 | 0.00 | 0.00 | 0.00 | 3.67 | 11.52 |
| 4-methyl-hexene | 0.00 | 0.00 | 0.00 | 0.00 | 0.00 | 0.00 | 0.00 | 0.00 | 0.00 | 0.00 |
| Total Flow, kg/hr | 30.00 | 100.00 | 2.58 | 100.00 | 48.01 | 100.00 | 0.72 | 100.00 | 31.87 | 100.00 |
| Pressure, kPa | 2500 | | 2500 | | 2500 | | 400 | | 438 | |
| Temperature, ° C. | 45.0 | | 35.0 | | 68.3 | | 46.7 | | 107.4 | |

TABLE 2

| | 1 Feed | | 2 EtOH feed | | 10 Side draw | | 11 Top Product | | 12 Bottom product | |
|---|---|---|---|---|---|---|---|---|---|---|
| | Mass Flow | Mass-% | Mass Flow | Mass-% | Mass Flow | Mass-% | Mass Flow | Mass-% | Mass Flow | Mass-% |
| EtOH | 0.00 | 0.00 | 3.56 | 100.00 | 3.74 | 7.30 | 0.02 | 0.24 | 0.01 | 0.03 |
| Isobutene | 1.70 | 5.67 | 0.00 | 0.00 | 0.02 | 0.04 | 0.06 | 0.88 | 0.00 | 0.00 |
| 2-Methyl-1-butene | 1.08 | 3.60 | 0.00 | 0.00 | 0.13 | 0.26 | 0.00 | 0.00 | 0.03 | 0.10 |
| 2-Methyl-2-butene | 1.94 | 6.48 | 0.00 | 0.00 | 1.52 | 2.96 | 0.00 | 0.00 | 0.60 | 2.27 |
| 2-Methyl-1-pentene | 0.90 | 3.00 | 0.00 | 0.00 | 0.02 | 0.04 | 0.00 | 0.00 | 0.12 | 0.45 |
| 2-Methyl-2-pentene | 0.93 | 3.09 | 0.00 | 0.00 | 0.03 | 0.07 | 0.00 | 0.00 | 0.78 | 2.96 |

TABLE 2-continued

| | 1 Feed | | 2 EtOH feed | | 10 Side draw | | 11 Top Product | | 12 Bottom product | |
|---|---|---|---|---|---|---|---|---|---|---|
| | Mass Flow | Mass-% | Mass Flow | Mass-% | Mass Flow | Mass-% | Mass Flow | Mass-% | Mass Flow | Mass-% |
| 2,3-Dimethyl-1-butene | 0.15 | 0.50 | 0.00 | 0.00 | 0.01 | 0.02 | 0.00 | 0.00 | 0.02 | 0.09 |
| 2,3-Dimethyl-2-butene | 0.08 | 0.28 | 0.00 | 0.00 | 0.00 | 0.00 | 0.00 | 0.00 | 0.11 | 0.43 |
| 2-Ethyl-1-butene | 0.03 | 0.10 | 0.00 | 0.00 | 0.00 | 0.00 | 0.00 | 0.00 | 0.00 | 0.01 |
| 3-Methyl-cis-2-pentene | 0.10 | 0.35 | 0.00 | 0.00 | 0.00 | 0.01 | 0.00 | 0.00 | 0.09 | 0.34 |
| 3-Methyl-trans-pentene | 0.24 | 0.81 | 0.00 | 0.00 | 0.00 | 0.01 | 0.00 | 0.00 | 0.20 | 0.75 |
| 1-Methylcyclopentene | 0.15 | 0.51 | 0.00 | 0.00 | 0.00 | 0.00 | 0.00 | 0.00 | 0.13 | 0.48 |
| ETBE | 0.00 | 0.00 | 0.00 | 0.00 | 0.02 | 0.04 | 0.00 | 0.00 | 2.99 | 11.31 |
| TAEE | 0.00 | 0.00 | 0.00 | 0.00 | 0.00 | 0.00 | 0.00 | 0.00 | 3.97 | 15.03 |
| THEE1 | 0.00 | 0.00 | 0.00 | 0.00 | 0.00 | 0.00 | 0.00 | 0.00 | 1.44 | 5.44 |
| THEE2 | 0.00 | 0.00 | 0.00 | 0.00 | 0.00 | 0.00 | 0.00 | 0.00 | 0.15 | 0.55 |
| THEE3 | 0.00 | 0.00 | 0.00 | 0.00 | 0.00 | 0.00 | 0.00 | 0.00 | 0.14 | 0.51 |
| Methyl-syclopentylether | 0.00 | 0.00 | 0.00 | 0.00 | 0.00 | 0.00 | 0.00 | 0.00 | 0.04 | 0.15 |
| i-Butane | 6.87 | 22.91 | 0.00 | 0.00 | 1.90 | 3.71 | 6.87 | 96.07 | 0.00 | 0.01 |
| n-Hexane | 7.14 | 23.81 | 0.00 | 0.00 | 0.30 | 0.58 | 0.00 | 0.00 | 7.15 | 27.07 |
| Benzene | 0.22 | 0.72 | 0.00 | 0.00 | 0.00 | 0.01 | 0.00 | 0.00 | 0.22 | 0.82 |
| i-Pentane | 7.80 | 25.99 | 0.00 | 0.00 | 43.34 | 84.53 | 0.20 | 2.81 | 7.58 | 28.69 |
| i-hexane | 0.65 | 2.18 | 0.00 | 0.00 | 0.21 | 0.42 | 0.00 | 0.00 | 0.66 | 2.49 |
| Total Flow, kg/h | 30.00 | 100.00 | 3.56 | 100.00 | 51.27 | 100.00 | 7.15 | 100.00 | 26.41 | 100.00 |
| Pressure, kPa | 1500 | | 1500 | | 1500 | | 400 | | 400 | |
| Temperature, ° C. | 25.0 | | 25.0 | | 65.9 | | 27.0 | | 95.8 | |

A comparison of the conversions of the various reactants with the corresponding results obtained by the TAME process described in WO 93/19031 indicates that the conversions of 2-Me-1-butene and 2-Me-2-butene are on the same level whereas the conversion of reacting $C_6$'s is clearly improved. The results are summarized in the following table:

TABLE 3

Conversion Comparison

| | Feed | Bottom | Distillate | Conversion |
|---|---|---|---|---|
| Present invention (methyl ethers) | | | | |
| 2-Me-1-butene | 1.52 | 0.04 | 0.00 | 0.98 |
| 2-Me-2-butene | 10.89 | 1.06 | 0.01 | 0.90 |
| $C_6$ reacting | 13.44 | 4.31 | 0.00 | 0.66 |
| Example 4 of WO 93/19031 | | | | |
| 2-Me-1-butene | 1.82 | 0.07 | 0.03 | 0.96 |
| 2-Me-2-butene | 11.67 | 1.32 | 0.06 | 0.88 |
| $C_6$ reacting | 11.75 | 5.74 | | 0.48 |
| Example 1 of WO 93/19031 | | | | |
| 2-Me-1-butene | 7.50 | 0.34 | | 0.95 |
| 2-Me-2-butene | 13.74 | 6.51 | | 0.50 |
| $C_6$ reacting | 6.91 | 4.94 | | 0.24 |

I claim:

1. A process for preparing tertiary alkyl ethers, comprising the steps of
    reacting $C_{4-7}$ isoolefins of an olefinic hydrocarbon feedstock with an alkanol in the presence of a catalyst in at least one reaction zone to form a reaction mixture containing a tertiary alkyl ether or a mixture of tertiary alkyl ethers,
    feeding the reaction mixture to a distillation column at a feed point between the bottom and the top of the column,
    subjecting said reaction mixture to distillation in the distillation column,
    recovering the alkyl ether(s) and $C_{5-7}$ hydrocarbons with the bottoms product of the distillation,
    withdrawing an azeotrope formed by unreacted $C_4$ hydrocarbons and said alkanol as an overhead product of the distillation,
    withdrawing from above the feed point of the reaction mixture a part of the liquid flow of the column to form a side drawoff, and
    recirculating the side drawoff to the reaction zone.

2. The process according to claim 1, wherein the reaction zone is placed in at least two reactors connected to the distillation column.

3. The process according to claim 1 or 2, wherein the side drawoff is cooled before being fed into the reaction zone.

4. The process according to claim 3, wherein the alkanol used in the etherification zone is separately fed into the reaction zone.

5. The process according to claim 1, wherein the fresh hydrocarbon feed stream and the side drawoff of the distillation are combined before the reaction zone to form a modified feed for the reaction zone.

6. The process according to claim 1, wherein the alkanol is methanol or ethanol or a mixture thereof.

7. The process according to claim 1, wherein the reaction mixture is heated before feeding into the distillation column.

8. The process according to claim 1, wherein the flow rate of the side drawoff amount is 10 to 500%, of the flow of the fresh hydrocarbon feed.

9. The process according to claim 8, wherein said flow rate is 50 to 200%.

10. The process according to claim 1, wherein said side drawoff is taken from a tray in said column which is located below trays in said column having alkanol k-values of less than 1.

11. The process according to claim 9 or 10, wherein said feed point for said reaction mixture is at a plate in said column having an alkanol k-value of greater than 1.

* * * * *